United States Patent
Hosny

(10) Patent No.: US 6,676,691 B1
(45) Date of Patent: Jan. 13, 2004

(54) STENT DELIVERY SYSTEM

(76) Inventor: Ayman A. Hosny, 2222 East St., #260, Concord, CA (US) 94520

( * ) Notice: Subject to any disclaimer, the term of this patent is extended or adjusted under 35 U.S.C. 154(b) by 74 days.

(21) Appl. No.: 09/820,386

(22) Filed: Mar. 28, 2001

(51) Int. Cl.[7] ................................................. A61F 21/06
(52) U.S. Cl. ..................................... 623/1.11; 623/1.35
(58) Field of Search .............................. 623/1.23, 1.11, 623/1.35, 1.12; 604/164.05

(56) References Cited

U.S. PATENT DOCUMENTS

| | | | |
|---|---|---|---|
| 4,994,071 A | | 2/1991 | MacGregor |
| 5,084,022 A | * | 1/1992 | Claude ........................ 604/164 |
| 5,632,763 A | | 5/1997 | Glastra |
| 5,669,924 A | | 9/1997 | Shaknovich |
| 5,720,735 A | | 2/1998 | Dorros |
| 5,755,771 A | | 5/1998 | Penn et al. |
| 5,879,324 A | * | 3/1999 | von Hoffmann ............. 604/49 |
| 5,938,645 A | * | 8/1999 | Gordon ....................... 604/264 |
| 6,033,434 A | | 3/2000 | Borghi |
| 6,033,435 A | | 3/2000 | Penn et al. |
| 6,056,775 A | | 5/2000 | Borghi et al. |
| 6,086,611 A | | 7/2000 | Duffy et al. |
| 6,099,560 A | | 8/2000 | Penn et al. |
| 6,117,117 A | | 9/2000 | Mauch |
| 6,183,509 B1 | * | 2/2001 | Dibie ......................... 623/1.35 |
| 6,309,379 B1 | * | 10/2001 | Willard et al. .............. 604/467 |
| 6,346,089 B1 | * | 2/2002 | Dibie ......................... 603/1.15 |
| 6,361,555 B1 | * | 3/2002 | Wilson ....................... 623/1.11 |
| 6,371,978 B1 | * | 4/2002 | Wilson ....................... 623/1.11 |
| 6,383,171 B1 | * | 5/2002 | Gifford et al. .............. 604/508 |
| 6,428,512 B1 | * | 8/2002 | Anderson et al. ...... 604/170.01 |
| 6,428,567 B2 | * | 8/2002 | Wilson et al. ............. 623/1.11 |
| 6,440,165 B1 | * | 8/2002 | Richter et al. ............. 623/1.35 |

* cited by examiner

*Primary Examiner*—David H. Willse
*Assistant Examiner*—Suzette J. Jackson
(74) *Attorney, Agent, or Firm*—Theodore J. Bielen, Jr.

(57) ABSTRACT

A stent delivery system including a stent unit having a first portion and second portion which are contiguous with one another. The first and second portions are expandable through angioplasty balloons. The first portion is constructed with a recess in its collapsed position to hold the second portion. The second portion extends or protracts from the first portion to allow the stent to deploy in a bifurcated vessel. The stent may be employed with a delivery sheath that has separable portions.

9 Claims, 4 Drawing Sheets

STENT DELIVERY SYSTEM

BACKGROUND OF THE INVENTION

The present invention to a novel stent delivery system in the treatment of occluded blood vessels.

Percutaneous transluminal coronary angioplasty (PTCA) has proven to be a successful technique in the treatment of stenotic arteries and vessels, particularly those found in the human heart. In fact in certain cases, this treatment has served as a substitute for coronary by-pass surgery. During PTCA procedures, a catheter is inserted through a large artery in the leg or arm of the patient and is directed into an occluded vessel, such as a coronary artery. The catheter also carries an inflatable balloon which forces open the obstruction, normally in the form of a plaque material. In addition to the use of such balloon angioplasty procedures, stents have been developed to maintain the dilated vessel in an open condition. The use of stents has prevented subsequent closures of vessels referred to as "restenosis", due to scarring, the accumulation of plaque and the like.

A particularly vexing situation occurs in vessels which include a branching arrangement. Such situation is referred to as a bifurcating vessel, i.e. where a main trunk vessel meets a side branch vessel. The angle between the main trunk vessel and the side branch is usually referred to a "carina". Carinas may be acute, orthogonal, or obtuse. In a bifurcating vessel situation, the side branch often includes lesions similar to that of the main trunk branch. Insertion of a stent in the main trunk vessel alone, following dilation, is not satisfactory, since the side branch lumen is blocked. Stents must be placed in the main trunk vessel as well as the side branch to properly rectify occluded vessels in a bifurcating vessel.

Systems have been proposed for stent placement in bifurcating vessel. For example, the U.S. Pat. Nos. 5,632,763; 5,669,924; 5,720,735; 6,033,434; 6,056,775; and 6,117,117 show stent devices and procedures in which separate stents are placed in the main trunk vessel as well as the side branch of a bifurcating vessel. In most cases, a pair of guide wires is employed to separately direct distinctive stents in each of the portions of the bifurcated vessel.

U.S. Pat. Nos. 4,994,071; 5,755,771; 6,033,435; 6,086,611; and 6,099,560 show stent systems in predilated bifurcating vessel situations which use forked stents. These forked stent derive from a main stent body and include pairs of end stents that are expandable from a side-by-side parallel configuration to an angular configuration for insertion into the main trunk vessel and side branch.

A stent system which is adaptable for use in a bifurcating vessels of varying angular configurations would be a notable advance in the field of percutaneous transluminal coronary angioplasty.

SUMMARY OF THE INVENTION

In accordance with the present invention a novel and useful stent system for emplacement in a branched vessel is herein provided.

The stent system of the present invention utilizes a stent unit having a first portion including a wall which forms a first lumen through the same. The first portion is constructed of material permitting the expansion of the wall between an initially collapsed configuration and an extended position. For example, the first portion of the stent unit may be composed of articulating stents which expand under pressure, a structure known in the art. Such change in configuration is accomplished by the use of mechanical forces applied to the first portion. In the latter case, expansion is achieved by the use of an expanding balloon used in angioplasty procedures.

A second portion is also included in the stent system of the present invention. The second portion possesses a wall forming a second lumen. The second portion is constructed of a material which is similar, but more rigid than, the material of the first portion. Thus, the second portion exhibits the same expansion characteristics, but expands under a higher applied pressure due to the nature of the construction material with respect to the first portion. The second lumen of the second portion communicates with the first lumen of the first portion. Also, the wall of the second portion is contiguous with the wall of the first portion. In this regard the first portion may be configured to form a recess which is at least partially occupied by the second portion when the stent unit is in its collapsed position. In addition, the wall of the first portion forming the recess may be constructed of a less rigid material than the remainder of the first portion. Such configuration permits the expansion of the recess portion of the first portion under a lower pressure than the remainder of the first portion of the stent unit. The second portion is also capable of unseating and protracting from the recess of the first portion, when the stent system is inserted in a bifurcating vessel, during expansion. In other words, at a relatively low applied pressure, without expansion of the first portion of the stent unit, the recess expands to unseat the second portion from the recess. Further application of pressure expands the remainder of the first portion. Finally additional pressure, expands the protracted second portion. In general, the main trunk or first passage of the bifurcating vessel would be occupied by the first portion of the stent unit while the second portion of the stent system would occupy the second passage or side branch of the bifurcating vessel.

An angioplasty balloons, having a bifurcated or tee configuration, may be incorporated into the stent system of the present invention. Also, other occlusion removal devices, such as those used in rotational arthrectomy techniques, are compatible with the system of the present invention, prior to deployment of the stent unit of the present invention. The operation of the stent system of the present invention will be more fully described hereinafter.

In addition to the stent unit above described, the stent system of the present invention further employs a stent delivery device in the form of a sheath having an external surface and a chamber or cavity therewithin. The sheath extends over the stent unit, resulting in the stent unit lying in the cavity of the sheath. The sheath is formed with an elongated body that terminates in an end portion. The end portion is split into first and second elements that are separable from one another. Thus, a gap may be formed between the first and second elements in this regard. In certain cases, the first and second elements of the end portion of the sheath may be formed from a material which is more flexible than the material forming the body of the sheath. Such flexibility may also be accomplished by thinning the first and second portions in the vicinity of the gap between the sheath. The sheath may also be constructed with first and second openings to pass first and second guide wires. Of course, the guide wires extend from the exterior of the body of the patient to the end portion of the sheath and through the first and second openings. In addition, it should be understood that, in a PTCA procedure, guide wires are placed or positioned in the bifurcating vessel, one in the main trunk and one in the side branch by initially entering the patient through an artery in the leg or arm by using conventional PTCA techniques. Guide wires are also positioned, in the present system, relative to the first and second portions of the stent unit such that one guide wire extends through the first lumen and the other guide wire extends through the second lumen of the same. The guide wires may be marked with indicia or coloration, which is visible externally to the body of the patient in order to keep track of the same during a PTCA procedure.

A catheter may be used to deliver the guide wires into the proper positions herein above described. The catheter may take the form of an elongated tube which includes first and second passageways terminating in first and second openings. The ends of the guide wires may be angled or bent to match the particular configuration of the bifurcating vessel prior to insertion. This permits the ends of the guide wires to be positioned in the proper portions of the bifurcating vessels. Normally, the guide wires are advanced one at a time, one wire to the main trunk followed by a second wire to the branched vessel. Of course, after positioning of the guide wires in the bifurcating vessel, the catheter is retracted from the vessel, leaving the guide wires in the proper position relative to the two portions of the bifurcating vessel. Guide wires also serve to direct the sheath for delivering the stent unit of the present invention into its proper position. That is to say, the stent unit is advanced along the guide wires within the sheath when the sheath is in place.

The present invention also entails a method for placing a stent in a bifurcating vessel in which a catheter is advanced to the bifurcating vessel using PTCA techniques. The catheter possesses two passageway terminating in two openings. The first guide wire is delivered to the main trunk followed by the delivery of a second guide wire to the branched vessel. The first guide wire utilizes the first passageway and first opening, while the second guide wire utilizes the second passageway and the second opening of the catheter. After the wire delivering catheter is retracted, and, following predilation or other plaque attenuation techniques, a sheath is extended to the bifurcating vessel site. The stent unit of the present invention lies in its collapsed position and is fitted with a deflated bifurcated angioplasty balloon. Then stent unit is then placed in the sheath and fitted over the guide wires, extending outside the body of the patient. Needless to say, the first guide wire passes through the first lumen of the stent unit while the second guide wire passes through the second lumen of the stent unit. The stent unit is advanced along the guide wires and within the sheath to the bifurcating vessel. Once the stent unit is positioned at a proper position at the bifurcating vessel, the first end portion of the sheath passes back over the stent unit by separation or peeling of the first and second elements of its end portion. The sheath is then removed from the area of the bifurcating vessel and, eventually, from the body of the patient. The stent unit is then positioned within the bifurcated vessel in its proper position along the guide wires such that the first portion lies in the main trunk and the second portion extends into the side branch. Such positioning takes place by at least partial expansion of the first and second portions of the stent unit by inflation of a bifurcated angioplasty balloon. Low pressure inflation first causes unseating and protraction of the second portion of the stent unit, relative to the recess of first portion. Higher pressure in the balloon expands the first portion. Finally, the second portion in expanded at an ever higher pressure in the balloon. The forked angioplasty balloon is then deflated and removed along the guide wires, which are also removed.

It may be apparent that a novel in useful stent delivery system and method for placing a stent unit in a bifurcated vessel has been hereinabove described.

It is therefore an object of the present invention to provide a stent delivery system and a method for placing a stent unit in a bifurcated vessel which is simple and reliable.

Another object of the present invention is to provide a stent delivery system and a method for placing a stent unit in a bifurcating vessel which employs many of the techniques known in prior PTCA treatments.

Another object of the present invention is to provide a stent delivery system and a method for placing a stent unit in a bifurcating vessel which utilizes a stent unit that very closely conforms to the configuration of a bifurcating vessel determined by the carina between the main trunk vessel and the side branch.

Yet another object of the present invention is to provide a stent delivery system and a method for placing a stent unit in a bifurcating vessel which is capable of deploying a stent in such bifurcating vessel using simplified techniques, thus reducing the trauma to the patient.

Another object of the present invention is to provide a stent delivery system in a method for placing a stent unit in a bifurcating vessel which is completely safe and maintains the patency of both branches of the bifurcating vessel.

The invention possesses other objects and advantages especially as concerns particular characteristics and features thereof which will become apparent as the specification continues.

BRIEF DESCRIPTION OF THE DRAWINGS

FIG. 2b is a sectional view of a stenotic coronary artery having a carina variation from that shown in FIG. 1 and FIG. 2a.

For a better understanding of the invention reference is made to the following detailed description of the preferred embodiments thereof which should taken in conjunction with the prior described drawings.

DETAILED DESCRIPTION OF THE PREFERRED EMBODIMENTS

Various aspects of the present invention will evolve from the following detailed description of the preferred embodiments thereof which should be referenced to the herein above delineated drawings.

Figure 1:
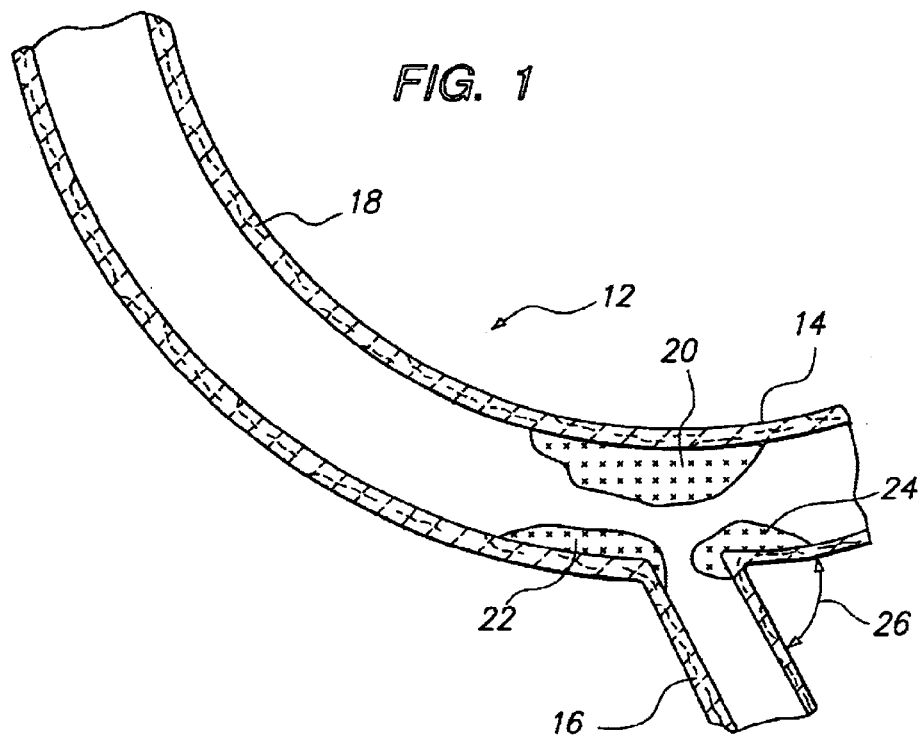
FIG. 1 is a sectional view showing a stenotic coronary bifurcating coronary artery.
Figure 2A:
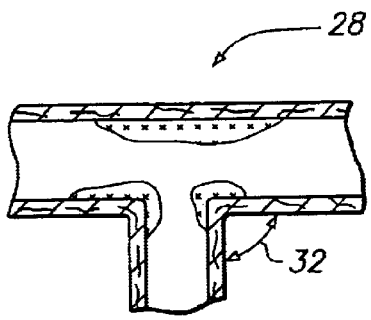
FIG. 2a is a sectional view representing a stenotic bifurcated coronary artery having a carina variation from that exhibited in FIG. 1.
Figure 2B:
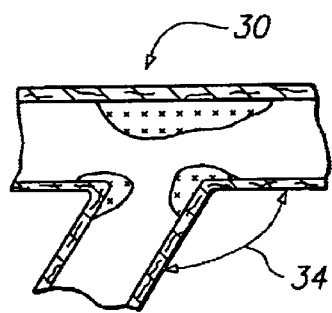

The invention as a whole includes a stent unit 10 which is intended for placement in a bifurcating vessel, depicted in section on FIG. 1. Vessel 12 may be a coronary artery, although other blood vessels would be suitable for the use with the system of the present invention. Coronary artery 12 possesses a main trunk 14 and a contiguous side branch 16. Occlusion or stenotic conditions are depicted in FIG. 1 in which atherosclerotic plaque deposits 20, 22, and 24 occlude a majority of the lumens of the main trunk 14 and the side branch 16 of bifurcating vessel 12. Directional arrow 26 represents the carina of bifurcating vessel 12, which is considered to be an acute angle. It should be noted, in general, that bifurcating vessels possess a variety of angles between the main trunks and side branches. For example, FIGS. 2A and 2B show bifurcating vessels 28 and 30. Vessel 28 exhibits an orthogonal carina, directional arrow 32, while bifurcating vessel 30 shows an obtuse carina, directional arrow 34. Both, vessels 28 and 30 show stenotic conditions due to atherosclerotic plaque.

Figure 3:
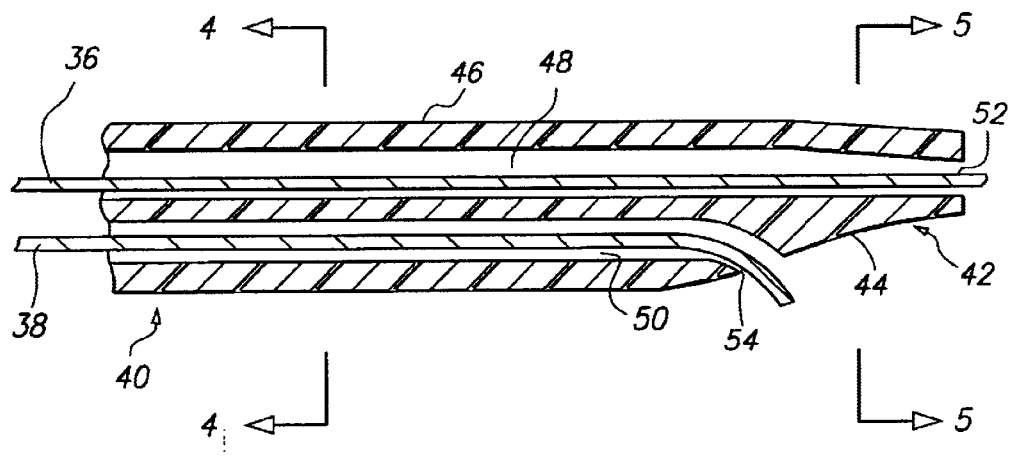
FIG. 3 is a sectional view of a catheter employed to deliver guide wires to the stenotic bifurcating coronary artery depicted in FIG. 1.
Figure 4:
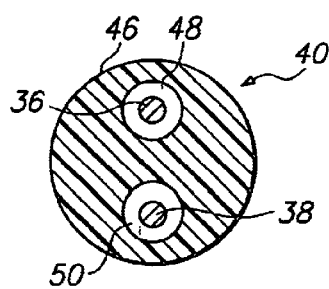
FIG. 4 is a sectional view taken along line 4—4 of FIG. 3.
Figure 5:
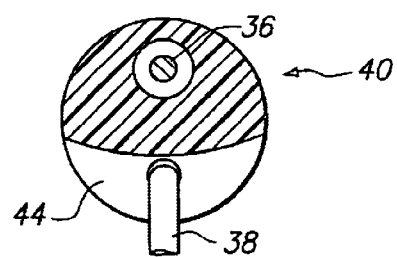
FIG. 5 is a sectional view taken along line 5—5 of FIG. 3.
Figure 6:
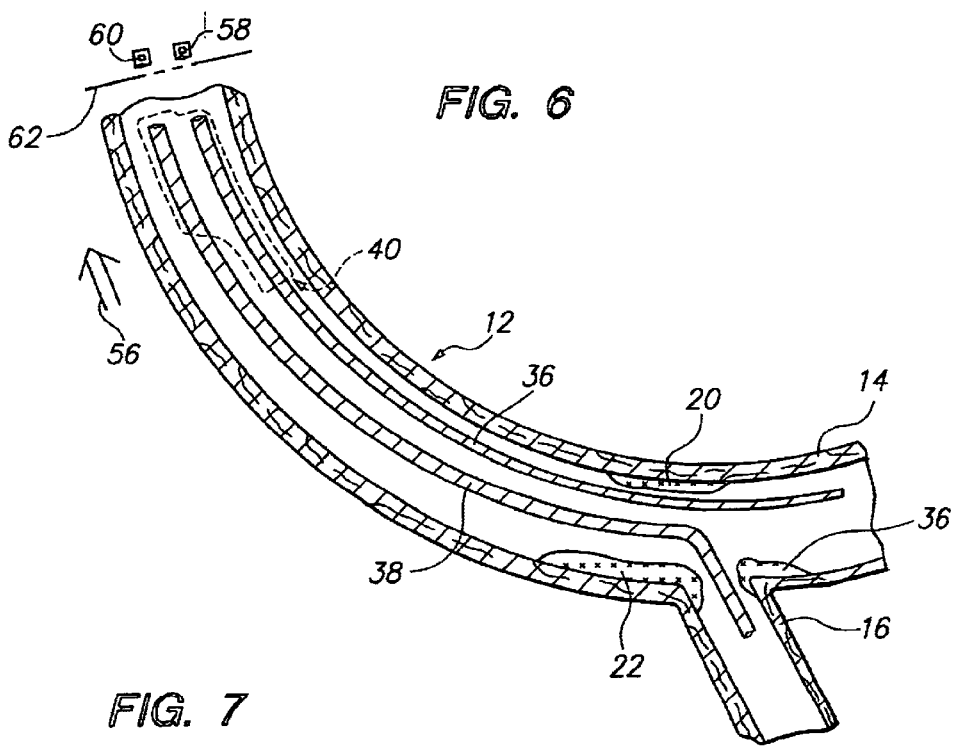
FIG. 6 is a sectional view of the bifurcating coronary artery of FIG. 1 in which guide wires have been placed in position, showing the retracting catheter in phantom.
Figure 11:
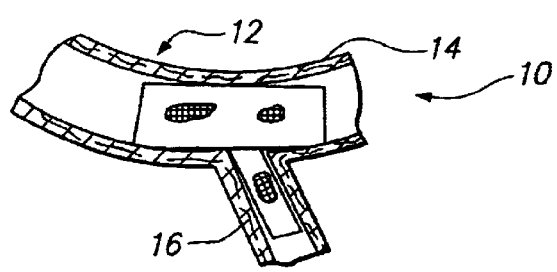
FIG. 11 is a sectional view of the bifurcated vessel showing a side elevational view of the stent unit of the present invention in place, and expanded fully with the guide wires and angioplasty balloons removed.

The system of the present invention utilizes several elements to place stent unit 10 within vessel 12, FIG. 11. With reference to FIG. 3, it may be observed that guide wires 36 and 38 are employed herein. Guide wires 36 and 38 may be formed from known materials such as stainless steel, titanium, and the like. Guide wire 36 and 38 are intended to be placed within main trunk 14 and side branch 16 of bifurcating vessel or artery 12. By using percutaneous transluminal coronary angioplasty (PTCA) techniques, guide wires 36 and 38 are extended placed into the body of the patient through a large artery in the, leg, groin, or arm areas, and like. Guide wires 36 and 38 are depicted as enlarged for the sake of clarity in the drawings. In the present application, a catheter 40 also extends from the exterior of the body of the patient to vessel 12. Of course, catheter 40 may be formed of any suitable biocompatable plastic material. Catheter 40 is constructed with a narrowed portion 42, having a slightly sloping surface 44. Catheter 40 is also formed with an outer surface 46 and inner passageways 48 and 50 terminating in openings 52 and 54, respectively. Openings 52 and 54 permit the passage of guide wires 36 and 38 from catheter 40, shown in FIGS. 3 and 5. As prior stated, catheter 40 and guide wires 36 and 38 pass through vessel 12 and are placed, one at a time, through catheter 40 and in the main trunk 14 and side branch 16 of vessel 12, respectively. FIG. 6 represents such placement. Following such placement, catheter 40 is withdrawn, depicted in phantom on FIG. 6, directional arrow 56. It should be noted that indicia 58 and 60 may be employed to distinguish guide wire 36 from guide wire 38 outside the body wall 66 of the patient. At this point, pre-dilation make take place to attenuate or clear plaque deposits 20,22 and 24 using conventional balloon angioplasty techniques. In addition, plaque deposits 20, 22, and 24 may be removed by other techniques, such as cardiac rotational arthrectomy.

Figure 7:
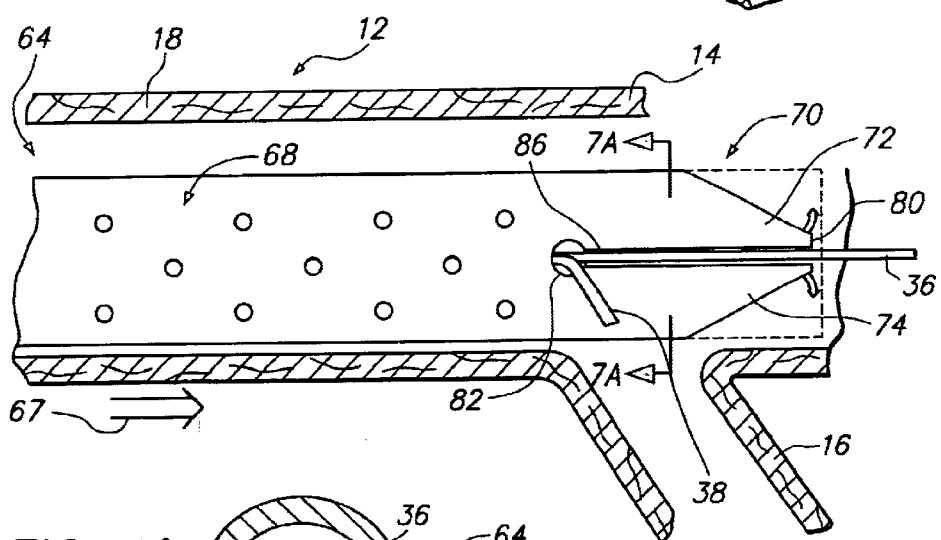
FIG. 7 is a sectional view of a portion of the bifurcating coronary artery of FIG. 1, in which pre-dilation has taken place and a sheath, capable of carrying the stent unit has been placed over guide wires, has been rotated 90° from its delivery position.
Figure 7A:
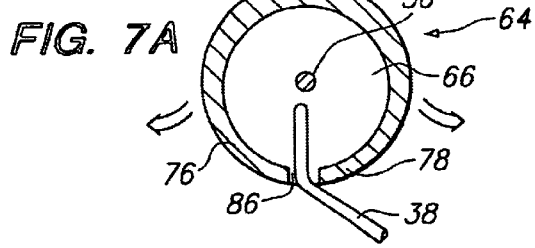
FIG. 7a is a sectional view taken along line 7a—7a of FIG. 7, without the stent unit therewithin being depicted, showing the sheath rotated 90° from FIG. 7.

Following removal of catheter 40, and attenuation or removal of atherosclerotic plaque deposits 20, 22, and 24, stent unit 10 may be shuttled or inserted within bifurcating vessel 12. A vehicle for carrying stent unit 10 externalizes in a sheath 64, depicted the form of a tube having an inner cavity or chamber 66, advanced in vessel 12, directional arrow 67. A plurality of perfusion openings 68 communicate with. chamber 66 and allow the flow of blood components through the same. Sheath 64 possesses an end portion 70 having a first element 72 and a second element 74 separated by gap 86. First and second elements 72 and 74 separate from one another in a peeling fashion. With respect to FIG. 7A, may be observed that such result is achieved by constructing sheath 70 with thinned side walls 76 and 78. In addition, end portion 72 may be constructed of a more flexible material than the remainder of sheath 64. Guide wires 36 and 38 extend through openings 80 and 82, respectively, and direct sheath to bifurcating region of vessel 12. It should be noted that sheath 70 has been rotated about 90° in FIGS. 7 and 7A within vessel 12 from the position depicted in FIG. 6. Although not illustrated in FIG. 7, stent unit 10 may be advanced therewithin once sheath 70 is positioned, such advancement of stent unit 10 will be discussed hereinafter.

Figure 8:
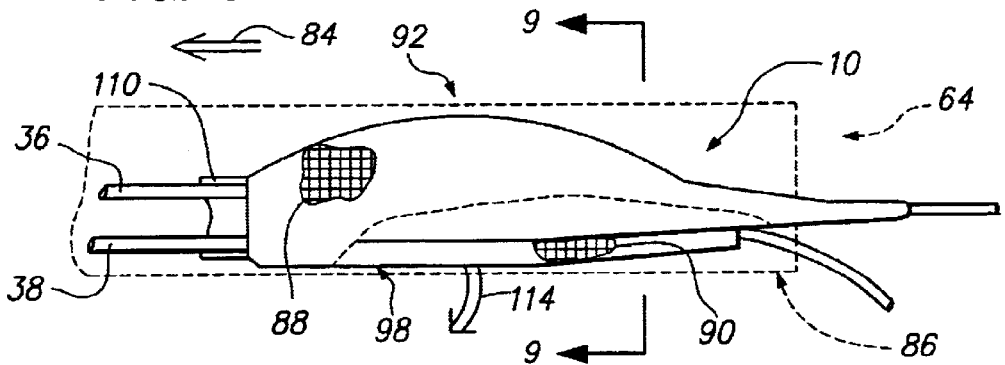
FIG. 8 is a side elevational view of the stent unit of the present invention in a collapsed, non-protracted position advanced into position within the sheath, depicted in phantom.
Figure 9:
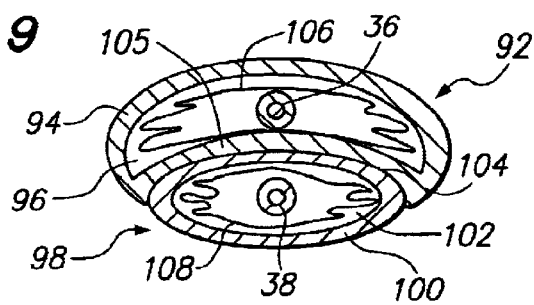
FIG. 9 is a sectional view taken along line 9—9 of FIG. 8.

Turning now to FIG. 8, it may be seen that stent unit 10 has been advanced within and is depicted within sheath 64 which has been partially retracted according to directional arrow 84. First and second elements 80 and 82 have separated to form an enlargement of gap 86. Stent unit 10 is composed of any known expandable material, such as a mesh, depicted by mesh parts 88 and 90 in FIG. 8. Stent unit 10 possesses a first portion 92 having a wall 94 forming a first lumen 96, and a second portion 98 including a wall portion 100 forming a lumen 102. Mesh parts 88 and 90 are associated with first portion 92 and second portion 90, respectively. Lumen 96 communicates with lumen 102. Mesh portion 88 of first portion 92 possesses less rigidly than mesh portion 90 of second portion 98. Most importantly, first portion 92 and second portion 98 of stent unit 10 assume a collapsed configuration, but are transformed to an expanded or enlarged configuration. FIGS. 8 and 9 depict stent unit 10 in a collapsed configuration in which first portion 92 forms a recess 104 which at least partially encloses second portion 98. Recess wall 105 is formed of an expandable material that is even less rigid than mesh part 88 of first portion 92. Angioplasty balloons forks or arms 106 and 108 lie within lumens 96 and 102 of first portion 92 and second portion 98 of stent unit 10, respectively. Angioplasty balloons arms 106 and 108 are filled through tube 110 in a conventional manner. That is to say, angioplasty balloon arms 106 and 108 configure to the shape of stent unit 10. Directional arrow 114 of FIG. 8 indicates the direction of protraction of second portion 98 from first portion 92 when angioplasty balloon 106 and 108 are further inflated.

Figure 10:
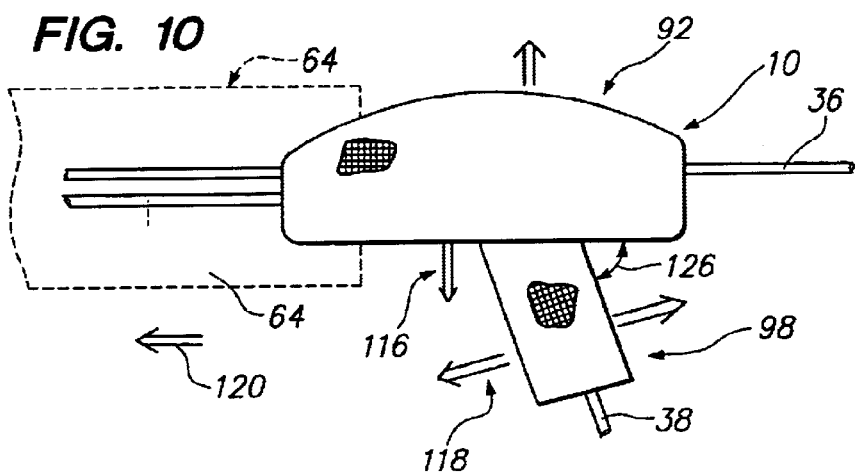
FIG. 10 is a side elevational view of the stent unit of the present invention in its protracted position, partially expanded, and also depicting the slightly retracted overlying sheath with its first and second elements of its end portion separated.

FIG. 10 shows a partially expanded stent unit 10 in which portion 98 has been protracted, directional arrow 116, and expanded, directional arrow 118. Sheath 64 has been almost completely retracted from stent unit 10 according to directional arrow 120. FIG. 11 depicts stent unit 10 in place within bifurcating vessel 12 following complete expansion of stent unit 10 and the removable of sheath 64, angioplasty balloons arms 106 and 108, and guide wires 36 and 38.

In operation, the user determines the type of carina configuration of an occluded vessel which is to be treated with the system of the present invention. Accordingly, stent unit 10 is chosen such that the final protraction of second portion 98 from first portion 92 forms an appropriate angle matching such carina, directional arrows 26 of FIG. 1, 32 of FIG. 2A, or 34 of FIG. 2B. That is to say, stent unit 10 may include the protraction of second portion 98 to accommodate orthogonal, acute or obtuse carinas. Using catheter 40, guide wires 36 and 38 are inserted into artery 12 and advanced to the bifurcating section, one at a time, depicted in FIG. 1, FIG. 2A or FIG. 2B. Guide wire 38 lies in main trunk portion 14, a short distance from the entrance to side branch vessel 16. Guide wire 36 is directed into branch vessel 16. When guide wires 36 and 38 are in place, catheter 40 is retracted. Guide wires 36 and 38 now lie in the configuration shown in FIG. 6. Following pre-dilation or other plaque removal techniques, a stent delivery system, is employed by passing sheath 64 over guide wires 36 and 38, directional arrow 67, FIG. 7. Stent unit 10 is then advanced over guide wires 36 and 38 within chamber 66 of sheath 64 in its collapsed position, and containing angioplasty balloon arms 106 and 108. Guide wires 36 and 38 serve to direct this combination of elements to bifurcating or branching vessel 12 using known PTCA techniques. Indicia 48 of 60 on wires and 38, respectively, function to track the identification of guide wires 36 and 38 relative to their positions in main trunk 14 and side branch 16 of vessel 12, respectively. In addition, guide wires 36 and 38 are kept from tangling with one another outside of body wall 62 during delivery of stent unit 10 to its intended position. When sheath 64 is located in the position depicted in FIG. 7 and stent unit 10 has been advanced along guide wires 36 and 38, sheath 64 is retracted according to directional arrow 84, FIG. 8. Such retraction causes first and second elements 72 and 74 of end portion 70 of sheath 64 to separate or peel, widening gap 86 therebetween and leaving stent unit 10 its proper position. Angioplasty balloon arms 106 and 108 are then inflated to cause second portion 98 to unseat and protract from recess 104 of first portion 92 at a low balloon pressure. Stent unit 10 is then maneuvered into bifurcating vessel 12, such that first portion 92 lies in main trunk vessel 14 and second portion 98 lies in branched vessel 16. Further inflation pressure in balloon arms 106 and 108 causes first portion 92 to expand. Second portion 98 finally expands with further pressure administered to balloon arms 106 and 108. Such differential expansion is due to the different construction of recess wall 105, first portion 92, and second portion 98. In addition, in the example illustrated, second portion 98 is protracted from first portion 92 to assume the configuration depicted in FIG. 10 with respect to an acute angle carina found in bifurcating vessel 12 of FIG. 8. Bifurcating balloon sections or arms 106 and 108 aid in the positioning of stent unit 10 within bifurcating vessel 12. In certain cases, angioplasty balloon arm 106 may be inflated first. However, the order of inflation of angioplasty balloon arms 106 and 108 are controlled by the configuration of stent unit 10 and the resistance to such expansion by bifurcating vessel 12. Following the positioning of stent unit 10 within bifurcating vessel 12, angioplasty balloon arms 106 and 108 are removed from vessel 12. Guide wires 36 and 38 are then removed from vessel 12 leaving stent unit 10 in place, as depicted in FIG. 11.

While in the forgoing, embodiments of the invention have been set forth in considerable detail for the purposes for making a complete disclosure of the invention, it may be apparent to those of skill in the art that numerous changes may be made such details without departing from the spirit and principles of the invention.

What is claimed is:
1. A stent system for emplacement in a branched vessel having first and second passages, comprising:
   a. a first portion, said first portion including a wall forming a first lumen therethrough, said first portion constructed of a material permitting the expansion of said wall from a collapsed configuration to an expanded position;
   b. a second portion, said second portion including a wall forming a second lumen, said second portion constructed of a material permitting the expansion of said wall from a collapsed configuration to an expanded and protracted configuration relative to said first portion, said first portion connecting to said second portion to form a stent unit, said first lumen communicating with said second lumen, said first portion forming a recess when said first portion assumes said collapsed configuration, said second portion at least partially occupying said recess, said second portion moved from and positioned outside said first portion recess when assuming said protracted configuration; and
   c. a sheath having an external surface and a chamber therewithin, said sheath extending over said stent unit to position said stent unit in said chamber, said sheath including an elongated body terminating in an end portion, said sheath end portion including first and second opening passing from the external surface of said sheath to said sheath chamber, said sheath end portion further including a first element and a second element, said first and second elements formed of a material more flexible than the material forming said elongated body of said sheath, said first element being separated from said second element to form a gap, said gap enlarging upon retraction of said sheath from said first and second portion.
2. The system of claim 1 which further comprises a first guide wire extending through said chamber of said sheath to said end portion of said sheath and through said first opening, and a second guide wire extending through said chamber of said sheath to said second end portion of said sheath and through said second opening.
3. The system of claim 2 in which said first guide wire passes through said first lumen of said first portion of said stent unit and said second guide wire passes through said second lumen of said second portion of said stent unit.
4. The system of claim 2 in which said first guide wire includes a first indicia and said second guide wire includes a second indicia.
5. A stent system for emplacement in a branched vessel having first and second passages, comprising:
   a. a first portion, said first portion including a wall forming a first lumen therethrough, said first portion constructed of a material permitting the expansion of said wall from a collapsed configuration to an expanded position;
   b. a second portion, said second portion including a wall forming a second lumen, said second portion constructed of a material permitting the expansion of said wall from a collapsed configuration to an expanded and protracted configuration relative too said first portion, said first portion connecting to said second portion to form a stent unit, said first lumen communicating with said second lumen;
   c. an inflatable member located in said lumen of said first portion, said inflatable member of said first portion capable of expanding said wall thereof;
   d. an inflatable member located in said lumen of said second portion, said inflatable member of said second portion capable of expanding said wall thereof, said inflatable member of said first portion being operable independently of said inflatable member of said second portion; and e. a sheath having an external surface and a chamber therewithin, said sheath extending over said stent unit to position said stent unit in said chamber, said sheath including an elongated body terminating in an end portion, said sheath end portion including first and second openings passing from the external surface of said sheath to said sheath chamber, said sheath end portion further including a first element and a second element, said first and second elements being formed of a material more flexible than the material forming said elongated body of said sheath, said first element being separated from said second element to form a gap, said gap enlarging upon retraction of said sheath from said first and second portions.

6. The system of claim 5 which further comprises a first guide wire extending through said chamber of said heath to said end portion of said sheath and through said first openings, and a second guide wire extending therethrough said chamber of said sheath to said second end portion of said sheath and through said second openings.

7. The system of claim 6 in which said first guide wire passes through said first lumen of said first portion of said stent unit and said second guide wire passes through said second lumen of said second portion of said stent unit.

8. A method of placing a stent in a bifurcating vessel of a subject, the bifurcated vessel having a main trunk and a connecting branch, comprising:

a. placing a first guide wire from the exterior of the subject into the main trunk of the bifurcating vessel, b. placing a second guide wire from the exterior of the subject into the connecting branch of the bifurcated vessel, c. positioning a stent unit having a first lumen over said first guide wire, and a second portion including a second lumen over said second guide wire, said stent unit first and second portions each including a wall constructed of a material permitting the expansion thereof from a collapsed configuration to an expanded configuration, said first portion further including a recess for nesting said second portion in said collapsed position, said second portion positioned outside said recess when assuming a protracted configuration relative to said first portion;

d. placing said stent unit and said first and second guide wires into a sheath;

e. directing said first and second guide wires into said main trunk and connecting branch of said bifurcated vessel, respectively, by employing a catheter;

f. positioning said stent unit at said bifurcated vessel;

g. independently inflating said first and second portions of stent unit to said expanded configuration of said first and second portions and to said protracted configuration of said second portion; and h. guiding said stent unit into said bifurcated vessel, said first portion positioned in said main trunk and said second portion positioned in said connecting branch.

9. The method of claim 8 which additionally includes the step of withdrawing said sheath from said stent unit prior to said step of guiding said stent unit unto said bifurcated vessel.

* * * * *